United States Patent [19]

Kompelien

[11] Patent Number: 4,558,595
[45] Date of Patent: Dec. 17, 1985

[54] CAPACITANCE MONITORING BRIDGE CIRCUIT FOR AN ENTHALPY RESPONSIVE DEVICE

[75] Inventor: Arlon D. Kompelien, Richfield, Minn.

[73] Assignee: Honeywell Inc., Minneapolis, Minn.

[21] Appl. No.: 717,777

[22] Filed: Mar. 29, 1985

[51] Int. Cl.$^4$ ............................................. G01W 1/02
[52] U.S. Cl. .................................... 73/336; 73/336.5; 324/61 R; 236/44 C; 165/21
[58] Field of Search ................... 374/35, 43; 73/336.5, 73/336; 62/176.6; 324/61 R; 165/21; 200/61.06; 236/44 C, 94

[56] References Cited

U.S. PATENT DOCUMENTS

| | | | |
|---|---|---|---|
| 2,991,653 | 7/1961 | Thompson | 73/336.5 |
| 3,177,427 | 4/1965 | Kuntz et al. | 324/61 R |
| 3,221,247 | 11/1965 | Samuelian | 324/60 R |
| 3,231,802 | 1/1966 | Myers | 236/94 |
| 3,280,618 | 10/1966 | Ballinger | 73/336.5 |
| 3,949,607 | 4/1976 | Nodolf | 73/336 |
| 4,431,962 | 2/1984 | Kompelien | 324/60 C |
| 4,449,188 | 5/1984 | Unoguchi et al. | 165/21 |
| 4,465,229 | 8/1984 | Kompelien | 73/336.5 |

FOREIGN PATENT DOCUMENTS

| | | | |
|---|---|---|---|
| 0120157 | 7/1983 | Japan | 374/35 |
| 0160856 | 9/1983 | Japan | 73/336.5 |

Primary Examiner—Charles Frankfort
Assistant Examiner—Thomas B. Will
Attorney, Agent, or Firm—Clyde C. Blinn

[57] ABSTRACT

An enthalpy control circuit has a humidity responsive capacitive element in one leg of a bridge circuit and a temperature responsive resistance element in another leg. The circuit is powered by a pulsating DC voltage of 1 kilohertz frequency for providing DC output, from an integrator connected to the output of the bridge circuit, indicative of enthalpy. A feedback from an integrator output to the bridge circuit is provided by chopping the DC output into appropriate AC for rebalance. Another feedback circuit around an amplifier provides a reference point compensated for offset voltages brought about by conditions such as temperature affecting circuit components.

7 Claims, 1 Drawing Figure

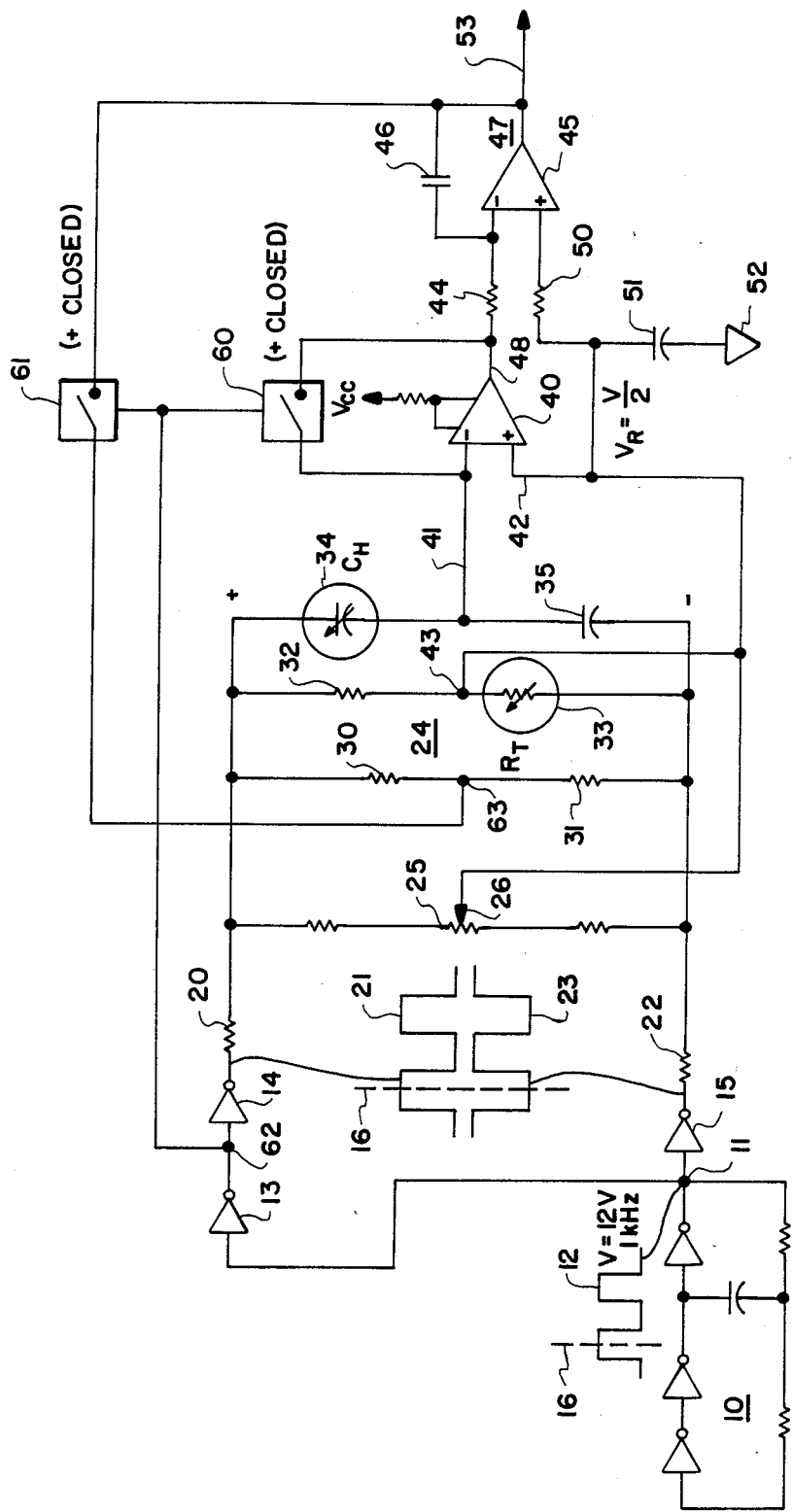

CAPACITANCE MONITORING BRIDGE CIRCUIT FOR AN ENTHALPY RESPONSIVE DEVICE

BACKGROUND AND SUMMARY OF THE INVENTION

While capacitor monitoring or measuring types of circuits for providing an output upon the change of the capacitance of one leg of a bridge circuit are old such as in the Arlon D. Kompelien U.S. Pat. No. 4,431,962, issued Feb. 14, 1984, such circuits are subject to the stability of the power supply and the relatively constant temperature of the components of the circuit. Enthalpy control devices having mechanical humidity responsive elements and a temperature responsive element have been used in air conditioning systems for years, such as a control device disclosed in the Keith M. Nodolf U.S. Pat. No. 3,949,607, issued Apr. 13, 1976.

The present invention is directed to an electrical circuit for an enthalpy responsive device having a humidity responsive element which changes in capacity in one leg of a bridge circuit and a resistance which changes in response to temperature in another leg. The circuit is fed by a pulsating DC voltage so the circuit output provides a DC signal indicative of enthalpy. To stabilize the output to make it minimally affected by changes in the frequency of the bridge power supply and changes in active amplifier components, a feedback from the output signal back to the bridge circuit is provided by a solid state switch which is closed during one half cycle of the bridge power supply and thus chops the DC output into an appropriate AC signal to be fed into the bridge circuit for stability. A further solid state switch feedback is provided around an intermediate amplifier to provide a reference voltage to a point between the capacitors of separate legs of the bridge circuit during one half cycle of the bridge supply so any signal change during the other half cycle can be properly amplified. This method of providing the capacitors reference voltage cancels effects of input offset voltage changes in the intermediate amplifier while still utilizing its high gain.

BRIEF DESCRIPTION OF THE DRAWINGS

The sole FIGURE is a circuit of the enthalpy control.

DESCRIPTION OF THE INVENTION

A bridge power supply or signal generator 10 provides a pulsating output of V=12 volts having a frequency of approximately 1 kilohertz at output terminal 11. As shown schematically by diagram at 12, the output is a square wave having a high output at least 50% of the time. After passing through two inverters or NOT gates 13 and 14, the pulsating voltage to resistor 20 is as shown by diagram at 21 and after passing through NOT gate 15, the pulsating voltage to resistor 22 is as shown at 23. At a given instant, such as 16, when the power supply voltage is high, voltage to resitor 20 is high (+) and voltage to resistor 22 is low (−). Connected between resistors 20 and 22 are four parallel branches in a bridge circuit 24. A first resistive branch contains a resistance 25 with an adjustable tap 26 for null balance and calibration. A second branch contains resistors 30 and 31 for a feedback signal. A third branch contains a resistor 32 and a temperature responsive resistance element 33 labeled as $R_T$. A fourth capacitive branch, which consists of two main bridge legs, contains a capacitive humidity responsive element or device 34 labeled $C_H$ and a fixed capacitor 35. The purpose of the three resistive branches is to properly effect changes in the pulsating voltages to the capacitive legs so that bridge balance is maintained. Element 33 is a thermistor or temperature responsive resistance element which varies in resistance depending upon the change in surrounding air temperature. Element 34 is a conventional humidity responsive polyimide type of capacitor which changes in capacity as the humidity in the surrounding air changes.

The output of bridge circuit 24 is connected to one input (−) of intermediate amplifier 40 by connection 41 from a terminal between the capacitive elements 34 and 35. A reference input, (+) to amplifier 40 is connected to a tap 43 between resistor 32 and the temperature responsive element 33 and to wiper 26 of the first branch by connection 42. A reference voltage capacitor 51, grounded at 52 is also connected to connection 42. The voltage developed by the flow of current from tap 26 and 43 to capacitor 51 provides a filtered (+) reference voltage of approximately Vr=V/2 on connection 42 for amplifier 40. By means of wiper 26 the calibration of bridge circuit 24 can be adjusted to provide a null for the desired conditions of $C_H$ (34) and $R_T$ (33) at the output of amplifier 40 on connection 48. Connection 48 is also connected to the input (−) of an amplifier 45 through a resistor 44 with capacitance 46 to operate as an integrator or integrator circuit 47 having a response relatively slow to the bridge power supply cycle period. A reference voltage input (+) is connected to integrator 47 from connection 42 through a resistor 50. The output 53 of integrator 47 is a filtered DC voltage indicative of the enthalpy as measured by the humidity element CH and the temperature element $R_T$.

To improve the operation of this circuit a pair of conventional solid state switches 60 and 61, which are switched by the voltage at terminal 62 to close when that voltage is positive. Switch 61 provides feedback for bridge circuit 24 by connecting the amplifier output 53 to a tap 63 of the balancing branch. The second switch 60 connects the output of amplifier 40 at 48 back to the input connection 41 to provide a reference voltage at this input. These switches 60 and 61 operate when the voltage at terminal 62 becomes positive to close momentarily for pulsating the DC voltage of amplifier output at 53 back to the bridge and to provide a reference voltage on connection 41 during one half cycle of power supply 10.

OPERATION OF THE INVENTION

Assuming that power supply 10 is operating to provide a pulsating voltage at 11 of twelve volts at one kilohertz, the voltage to resistors 20 and 22 would pulse whereby the upper portion of bridge circuit 24 would be at approximately twelve volts positive and the lower portion at near ground or zero voltage in an alternating manner. If we were to assume that bridge circuit 24 is balanced by the calibration potentiometer upon positioning wiper 26, the output at 41 to amplifier 40 would be at the reference voltage and the output integrator at 53 would be at V/2 or 6 volts.

Assuming an increase in humidity, the moisture responsive element 34 would increase in capacitance, and upon the voltage being at the particular instant selected shown by the dotted line 16, the upper side of bridge 24 would be plus and the lower side would be near ground with the 12 volts being distributed across the bridge to raise the voltage level of the output at 41 which would cause the output of amplifier 40 at 48 to drop and the output of the integrator at 53 to increase. Upon a reversal of the voltage to the bridge circuit on the next half cycle of the power supply, the lower side of the bridge would be plus 12 volts and simultaneously the switch 60 would be closed to hold the output of the bridge circuit at 41 at the output of the amplifier 40.

At the same time switch 61 closes to connect the output of the integrator to terminal 63 of one branch of the bridge to raise the voltage on both the upper and lower sides of the bridge of bridge 24, assuming that the voltage of 53 had increased. Upon a subsequent reversal of the power supply when the switches open and the upper side is near a positive 12 volts, not as much change occurs in the voltage rise on the upper side 25 as in the voltage drop on the lower side. This is reflected in the output at 41 and the integrator 47 would so respond. After a repetition of the power supply cycles, the feedback to bridge 24 through switch 61 would balance out the effect of the change in capacitance of element 34 until the output of the bridge at 41 during the open switch state would again be at the reference potential of amplifier 40 to have no effect in changing the output of the integrator at 53 whereby the voltage at 53 would provide a DC voltage indicative of the change in the effect of moisture on element $C_H$.

Obviously, a change in the reference voltage at 42 would have a similar effect upon the output of amplifier 40; therefore, upon a change in the air temperature to effect the resistance of element $R_T$, a similar output would be provided from amplifier 40 to result in a change of the output of the integrator which would be effective to rebalance the bridge circuit through switch 61.

By the same token, a decrease in the moisture content surrounding element $C_H$ would result in less capacitance to decrease the value of the bridge output at 41 with respect to the reference voltage to result in an increase in the output of the intermediate amplifier and thus a decrease in the output of the integrator. The feedback through switch 61 would have the reverse effect upon the balance of the bridge circuit until the bridge 24 was in balance and a negative voltage would be provided at output 53 indicative of a decrease in the moisture content and thus a change in the enthalpy.

Switch 60 provides a feedback to bring the input to amplifier 40 to the voltage of the reference 42 plus the internal input offset voltage of the amplifier during one half cycle to establish the reference for measuring the change from bridge 24 on the next half cycle. This compensates for variations in the input offset voltage of the amplifier due to temperature changes, aging, etc.

By a combination of the effects of elements $R_T$ for temperature and $C_H$ for humidity, the output of the integrator 47 provides a DC voltage indicative of the enthalpy of the air.

The embodiments of the invention in which an exclusive property or right is claimed are defined as follows:

1. In a control circuit comprising
moisture responsive capacitance means having a capacitance which varies with the amount of humidity in the surrounding air,
bridge circuit means having an input power circuit and an output circuit for providing an output when said bridge circuit means is unbalanced,
means connecting said moisture responsive means in one branch of said bridge circuit,
bridge power supply means providing a pulsating DC voltage at a predetermined frequency and connected to said input power circuit,
amplifier circuit means having a reference input circuit,
integrator circuit means having an input circuit for receiving a pulsating signal and an output circuit providing a DC output voltage,
means connecting said output circuit of said bridge circuit to said input circuit of said integrator circuit means through said amplifier circuit means whereby said DC voltage is indicative of humidity,
first feedback circuit means comprising switch means synchronized with said predetermined frequency connecting the DC output voltage of said integrator circuit means to said bridge circuit means for providing a voltage to balance said bridge circuit means.

2. The invention of claim 1 comprising
temperature responsive impedance means having an impedance which varies with the temperature of the surrounding air, and
means connecting said temperature responsive impedance means in a second branch of said bridge circuit means whereby said DC output voltage of said bridge circuit means is indicative of the enthalpy of the air.

3. The invention of claim 2 wherein
said one branch contains a fixed capacitance with said output between said fixed capacitance and said moisture responsive capacitance means,
said second branch contains a fixed impedance means and said temperature responsive means with an output between said fixed impedance means and said temperature responsive impedance, and
circuit means connecting said output of said second branch to said reference input of said amplifier and through a bias voltage capacitance means to ground for providing a bias voltage for said amplifier.

4. The invention of claim 3 comprising
a third branch of said bridge circuit containing an adjustable tapped resistance element connected through said bias voltage capacitance for calibrating said control circuit.

5. The invention of claim 4 comprising
second feedback circuit means comprising switch means synchronized with said predetermined frequency connected from an output of said amplifier means to said reference input circuit for bringing said input to said amplifier to zero on alternate half cycles of said frequency.

6. The invention of claim 2 wherein
said first feedback circuit means comprises a fourth branch of said bridge circuit means made of a tapped resistance circuit for providing a voltage to said bridge circuit means to offset said voltage of said output of said bridge circuit.

7. The invention of claim 2 wherein the time response of said integrator circuit means is much slower than said predetermined frequency period whereby said feedback voltage to said bridge circuit remains substantially the same throughout said power supply mean cycle.

* * * * *